(12) United States Patent
Chimmalgi et al.

(10) Patent No.: US 10,257,918 B2
(45) Date of Patent: Apr. 9, 2019

(54) SYSTEM AND METHOD FOR LASER-SUSTAINED PLASMA ILLUMINATION

(71) Applicant: KLA-Tencor Corporation, Milpitas, CA (US)

(72) Inventors: Anant Chimmalgi, San Jose, CA (US); Sebaek Oh, Millbrae, CA (US); Joshua Wittenberg, Fremont, CA (US); Lauren Wilson, San Jose, CA (US); Rahul Yadav, Sunnyvale, CA (US); Ilya Bezel, Mountain View, CA (US); Michael Navone, Cupertino, CA (US); Anatoly Shchemelinin, Bozeman, MT (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 15/274,956

(22) Filed: Sep. 23, 2016

(65) Prior Publication Data

US 2017/0094765 A1 Mar. 30, 2017

Related U.S. Application Data

(60) Provisional application No. 62/233,980, filed on Sep. 28, 2015.

(51) Int. Cl.
*H05G 2/00* (2006.01)
*G01N 23/04* (2018.01)
(Continued)

(52) U.S. Cl.
CPC ............. *H05G 2/008* (2013.01); *G01N 23/04* (2013.01); *G02B 6/0005* (2013.01);
(Continued)

(58) Field of Classification Search
CPC .... G01N 23/04; G02B 6/0005; G02B 6/0006; G02B 23/2469; G02B 27/1006;
(Continued)

(56) References Cited

U.S. PATENT DOCUMENTS 6,307,913 B1 10/2001 Foster et al.
6,382,957 B1 * 5/2002 Early ..................... F02P 23/04
123/143 B
(Continued)

FOREIGN PATENT DOCUMENTS

CN 203324186 U 12/2013
CN 104242021 A 12/2014
(Continued)

OTHER PUBLICATIONS

U.S. Appl. No. 15/187,590, filed Jun. 20, 2016, Matthew Derstine.
(Continued)

*Primary Examiner* — Taeho Jo
(74) *Attorney, Agent, or Firm* — Suiter Swantz pc llo

(57) ABSTRACT

An illumination pump source is disclosed. The illumination pump source includes a set of power sources configured to generate a set of laser beams, with at least some of the set of laser beams configured to include illumination having different wavelengths. The illumination pump source also includes an optical fiber. The illumination pump source also includes one or more optical elements, the one or more optical elements configured to couple the illumination from at least some of the laser beams to one or more regions of the optical fiber.

43 Claims, 10 Drawing Sheets

(51) Int. Cl.
  *G02B 6/02* (2006.01)
  *F21V 8/00* (2006.01)
  *G02B 27/14* (2006.01)
  *G02B 6/42* (2006.01)
  *G02B 6/028* (2006.01)

(52) U.S. Cl.
  CPC ......... *G02B 6/0006* (2013.01); *G02B 6/0008* (2013.01); *G02B 6/028* (2013.01); *G02B 6/02042* (2013.01); *G02B 6/4215* (2013.01); *G02B 27/141* (2013.01)

(58) Field of Classification Search
  CPC .... G02B 27/141; G02B 6/0008; G02B 6/003; G02B 6/02042; G02B 6/028; G02B 6/353; G02B 6/4215; G02B 7/021; H05G 2/008
  USPC ...................................................... 250/358.1
  See application file for complete search history.

(56) References Cited

U.S. PATENT DOCUMENTS

| | | | | |
|---|---|---|---|---|
| 6,428,307 B1 * | 8/2002 | Early | ................. | F02P 23/04 123/143 B |
| 6,447,537 B1 | 9/2002 | Hartman | | |
| 6,676,402 B1 * | 1/2004 | Early | ................. | F02P 23/04 123/143 B |
| 8,517,585 B1 | 8/2013 | Bezel et al. | | |
| 8,698,399 B2 | 4/2014 | Bezel et al. | | |
| 9,719,932 B1 * | 8/2017 | Shaughnessy | ..... | G01N 21/9501 |
| 2002/0093653 A1 | 7/2002 | Detalle et al. | | |
| 2002/0176677 A1 * | 11/2002 | Kumar | .............. | C03B 37/01222 385/126 |
| 2004/0057475 A1 | 3/2004 | Frankel et al. | | |
| 2006/0204190 A1 * | 9/2006 | Ranka | ................ | G02B 6/02009 385/123 |
| 2007/0001131 A1 * | 1/2007 | Ershov | ................. | H05G 2/003 250/503.1 |
| 2007/0228300 A1 * | 10/2007 | Smith | ................. | B82Y 10/00 250/504 R |
| 2008/0017801 A1 * | 1/2008 | Fonnenkov | ............ | B82Y 10/00 250/354.1 |
| 2009/0032740 A1 * | 2/2009 | Smith | ................. | B82Y 10/00 250/503.1 |
| 2009/0066934 A1 * | 3/2009 | Gao | ................... | G01N 15/1463 356/73 |
| 2009/0262262 A1 * | 10/2009 | Itoh | ......................... | G03B 21/14 348/760 |
| 2010/0142041 A1 * | 6/2010 | Berman | ............. | G02B 21/0032 359/385 |
| 2010/0193710 A1 | 8/2010 | Wakabayashi et al. | | |
| 2010/0228132 A1 * | 9/2010 | Brennan | .............. | A61B 5/0066 600/478 |
| 2010/0277804 A1 * | 11/2010 | Galvanauskas | .... | G02B 27/1006 359/583 |
| 2011/0181191 A1 * | 7/2011 | Smith | ................... | B82Y 10/00 315/149 |
| 2011/0204265 A1 * | 8/2011 | Smith | .................... | B82Y 10/00 250/503.1 |
| 2011/0268141 A1 * | 11/2011 | Nakatate | ............ | A61B 1/00163 372/6 |
| 2011/0291566 A1 * | 12/2011 | Bezel | ....................... | G21B 1/23 315/111.21 |
| 2011/0310475 A1 * | 12/2011 | Iketaki | ............... | G01N 21/6458 359/388 |
| 2012/0008139 A1 * | 1/2012 | Miziolek | ............... | G01N 21/718 356/318 |
| 2013/0010353 A1 * | 1/2013 | Berman | ............. | G02B 21/0032 359/385 |
| 2013/0106275 A1 | 5/2013 | Chimmalgi et al. | | |
| 2013/0284943 A1 * | 10/2013 | Brukilacchio | ....... | A61B 1/0653 250/458.1 |
| 2013/0342825 A1 * | 12/2013 | Chimmalgi | ........ | G01N 21/8806 356/51 |
| 2014/0117258 A1 * | 5/2014 | Smith | .................... | B82Y 10/00 250/492.2 |
| 2014/0153922 A1 * | 6/2014 | Ryf | ..................... | H04B 10/2581 398/44 |
| 2014/0240951 A1 * | 8/2014 | Brady | ..................... | F21V 13/08 362/19 |
| 2014/0319376 A1 * | 10/2014 | Pratt | ..................... | G01J 3/4406 250/458.1 |
| 2015/0042979 A1 * | 2/2015 | Chimmalgi | ........ | G01N 21/8806 356/51 |
| 2015/0048741 A1 | 2/2015 | Shortt et al. | | |
| 2015/0049778 A1 | 2/2015 | Shchemelinin et al. | | |
| 2015/0109759 A1 * | 4/2015 | Sugano | ................ | A61B 1/0669 362/84 |
| 2015/0201483 A1 | 7/2015 | Bezel et al. | | |
| 2015/0268400 A1 | 9/2015 | Chimmalgi et al. | | |
| 2015/0289353 A1 * | 10/2015 | Smith | ................... | B82Y 10/00 250/504 R |
| 2015/0332908 A1 * | 11/2015 | Blondia | .................. | H01J 61/16 313/111 |
| 2015/0333471 A1 * | 11/2015 | Chimmalgi | .......... | G02B 6/4296 250/504 R |
| 2015/0357179 A1 | 12/2015 | Wilson et al. | | |
| 2016/0005588 A1 * | 1/2016 | Park | ..................... | G02B 27/141 313/231.31 |
| 2016/0057845 A1 * | 2/2016 | Smith | ................... | B82Y 10/00 250/504 R |
| 2016/0131885 A1 * | 5/2016 | Nakayama | ......... | G01N 21/6428 250/458.1 |

FOREIGN PATENT DOCUMENTS

WO  2014098647 A1  6/2014
WO  2014168519 A1  10/2014

OTHER PUBLICATIONS

International Search Report dated Jan. 6, 2017 for PCT/US2016/053952.

* cited by examiner

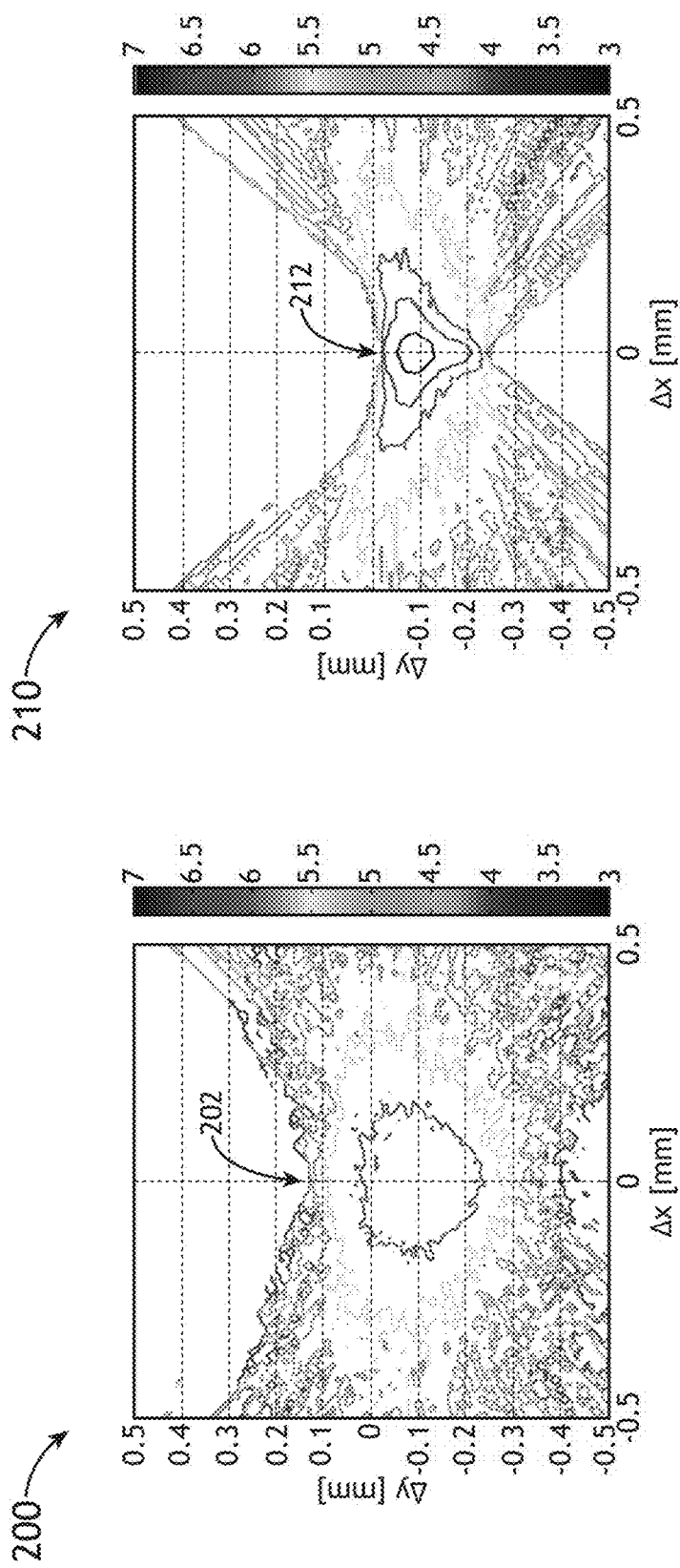

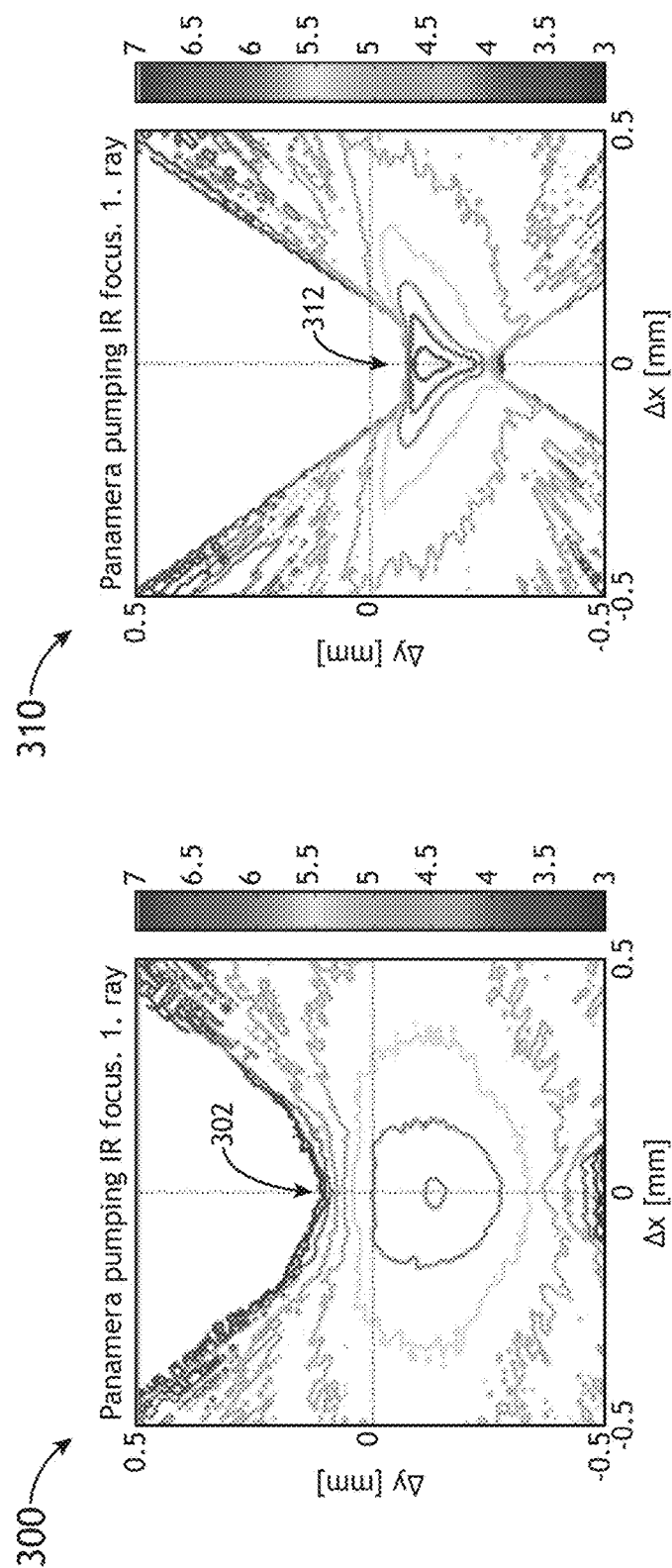

SYSTEM AND METHOD FOR LASER-SUSTAINED PLASMA ILLUMINATION

PRIORITY

The present application claims priority under 35 U.S.C. § 119(e) to U.S. Provisional Patent Application Ser. No. 62/233,980, entitled SELECTIVE LASER WAVELENGTH MIXING FOR PLASMA IGNITION, TEMPERATURE, AND SHAPE OPTIMIZATION, filed Sep. 28, 2015, naming Anant Chimmalgi, Sebaek Oh, Joshua Wittenberg, Lauren Wilson, Rahul Yadav, Ilya Bezel, Mike Navone, and Anatoly Shchemelinin as inventors, which is incorporated herein by reference in the entirety.

TECHNICAL FIELD

The present invention generally relates to plasma-based light sources, and, in particular, to a pump source for igniting and sustaining a plasma of a plasma-based light source.

BACKGROUND

As the demand for integrated circuits having ever-smaller device features continues to increase, the need for improved illumination sources used for inspection of these ever-shrinking devices continues to grow. One such illumination source includes a laser-sustained plasma light source. Laser-sustained plasma (LSP) light sources are capable of producing high-power broadband light. Laser-sustained light sources operate by focusing laser radiation into a gas volume in order to excite the gas, such as argon or xenon, into a plasma state, which is capable of emitting light. This effect is typically referred to as "pumping" the plasma.

Laser-sustained plasma illumination sources known in the art employ a pump source that emits a high-absorption laser wavelength or set of wavelengths to ignite a plasma. Laser pump wavelength is a critical parameter for igniting the plasma and achieving higher amounts of collectible power. To optimize collectible output from the plasma, wavelengths used for plasma ignition and wavelengths used to sustain the plasma are often different.

However, typical illumination pump sources are not capable of altering the wavelength, or set of wavelengths, between the ignition and sustaining phases of plasma source operation. Additionally, plasma illumination sources typically collect illumination only from the center of the plasma. Increasing power to the pump illumination source above a certain threshold results in saturation of collectible power, and only a fraction of the illumination output from the plasma is collected.

As such, it would be desirable to provide a system and method for curing the shortcomings of previous approaches such as those identified above.

SUMMARY

An illumination pump source is disclosed, in accordance with one or more embodiments of the present disclosure. In one illustrative embodiment, the illumination pump source includes a set of power sources configured to generate a set of laser beams. In another illustrative embodiment, at least some of the set of laser beams are configured to include illumination having different wavelengths. In another illustrative embodiment, the illumination pump source also includes an optical fiber. In another illustrative embodiment, the illumination pump source also includes one or more optical elements. In another illustrative embodiment, the one or more optical elements are configured to couple the illumination from at least some of the laser beams to one or more regions of the optical fiber.

A method for igniting and sustaining a plasma is disclosed, in accordance with one or more embodiments of the present disclosure. In one illustrative embodiment, the method includes generating a plurality of laser beams with a plurality of power sources, wherein at least some of the power sources emit laser beams having different wavelengths. In another illustrative embodiment, the method includes coupling at least some of the plurality of laser beams with one or more optical elements to one or more regions of an optical fiber. In another illustrative embodiment, the method includes adjusting the output of one or more of the plurality of power sources via one or more operational parameters of the plurality of power sources.

A system for imaging a sample with laser-sustained plasma illumination is disclosed, in accordance with one or more embodiments of the present disclosure. In one illustrative embodiment, the system includes an illumination pump source subsystem for igniting and sustaining a plasma. In another illustrative embodiment, the illumination pump source subsystem includes a plurality of power sources configured to generate a plurality of laser beams. In another illustrative embodiment, at least some of the power sources emit laser beams containing illumination having different wavelengths. In another illustrative embodiment, the illumination pump source subsystem includes an optical fiber. In another illustrative embodiment, the illumination pump source subsystem includes one or more optical elements. In another illustrative embodiment, the one or more optical elements are configured to couple the illumination from at least some of the laser beams to different regions of the optical fiber. In another illustrative embodiment, the coupled illumination from at least some of the laser beams forms a pump illumination. In another illustrative embodiment, the system includes a broadband illumination source subsystem. In another illustrative embodiment, the broadband illumination source subsystem includes one or more illumination optical elements configured to direct at least a portion of the pump illumination. In another illustrative embodiment, the broadband illumination source subsystem includes a gas containment element for containing a volume of gas. In another illustrative embodiment, the one or more illumination optical elements are configured to sustain a plasma within a volume of gas in the gas containment element by directing at least a portion of the pump illumination along a pump path to one or more focal spots within the volume of gas. In another illustrative embodiment, the broadband illumination source subsystem includes one or more collection optical elements configured to collect broadband illumination emitted by the plasma along a collection path. In another illustrative embodiment, the system includes a sample stage for securing one or more samples. In another illustrative embodiment, the system includes an imaging subsystem. In another illustrative embodiment, the imaging subsystem includes a detector. In another illustrative embodiment, the imaging subsystem includes an objective. In another illustrative embodiment, the objective is configured to collect illumination from a surface of the sample and focus the collected illumination via a collection pathway to the detector to form an image of at least a portion of the surface of the one or more samples.

It is to be understood that both the foregoing general description and the following detailed description are exemplary and explanatory only and are not necessarily restrictive of the present disclosure. The accompanying drawings, which are incorporated in and constitute a part of the characteristic, illustrate subject matter of the disclosure. Together, the descriptions and the drawings serve to explain the principles of the disclosure.

BRIEF DESCRIPTION OF THE DRAWINGS

The numerous advantages of the disclosure may be better understood by those skilled in the art by reference to the accompanying figures in which:

FIG. 2A illustrates graphical data of laser pumping a plasma through an optical fiber, in accordance with one or more embodiments of the present disclosure.

FIG. 2B illustrates graphical data of laser pumping a plasma through an optical fiber, in accordance one or more embodiments of with the present disclosure.

FIG. 3A illustrates graphical data of laser pumping a plasma through an optical fiber, in accordance with one or more embodiments of the present disclosure.

FIG. 3B illustrates graphical data of laser pumping a plasma through an optical fiber, in accordance with one or more embodiments of the present disclosure.

DETAILED DESCRIPTION OF THE INVENTION

Figure 1A:
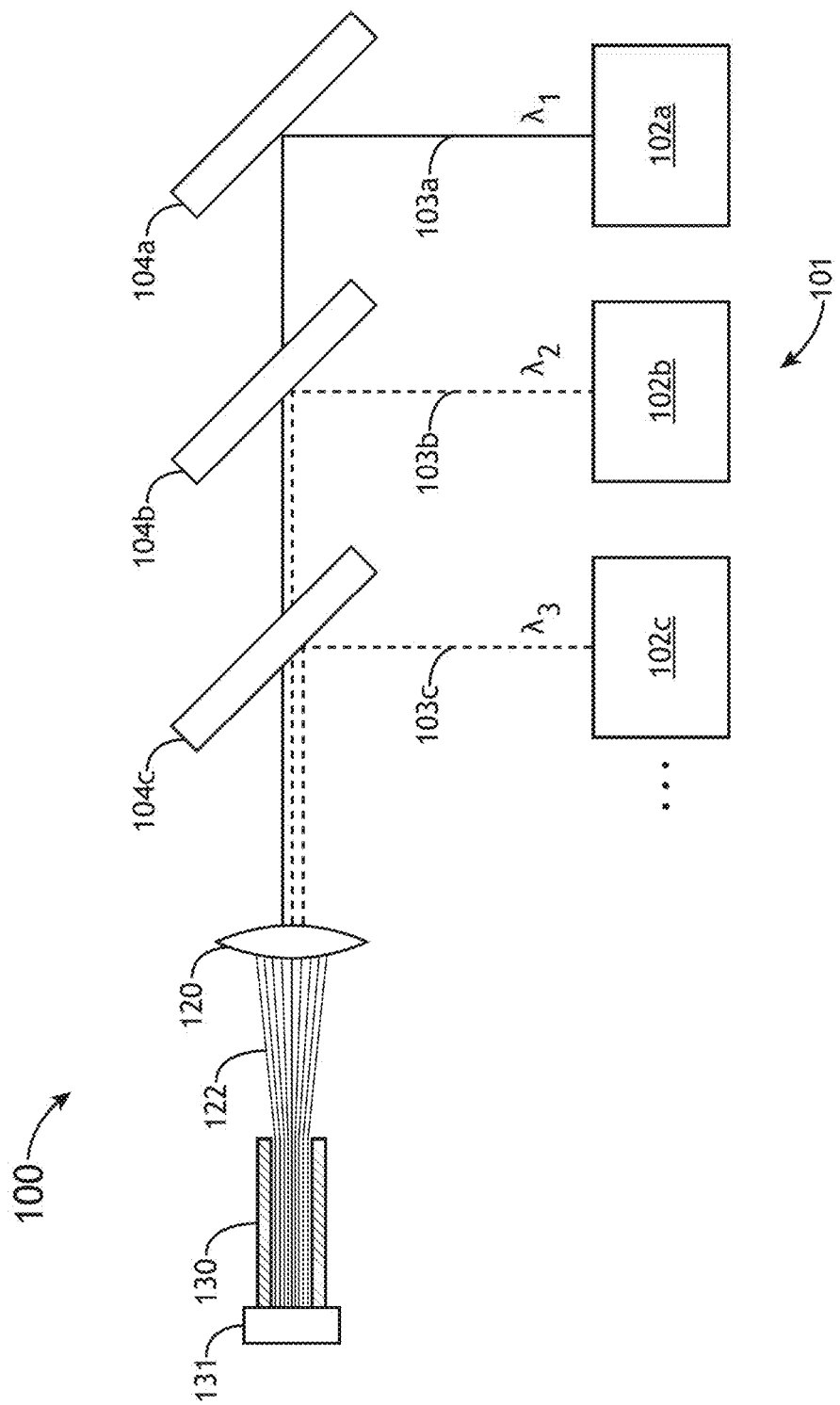
FIG. 1A illustrates an illumination pump source, in accordance with one or more embodiments of the present disclosure.

Reference will now be made in detail to the subject matter disclosed, which is illustrated in the accompanying drawings.

FIGS. 1A-5 generally illustrate a system and method for sustaining a plasma of a laser-sustained plasma illumination source, in accordance with one or more embodiments of the present disclosure.

Embodiments of the present disclosure are directed towards an illumination pump source including a set of power sources to generate multiple laser beams having different wavelengths.

It is noted that igniting and sustaining the plasma can be carried out at lower laser power in cases where the gas and/or plasma display strong absorption characteristics than in cases where the gas and/or plasma is weakly absorptive of the pump illumination. However, in the case of a plasma displaying strong absorption, the absorbed light may cause the plasma to increase in size and saturate in brightness.

Additionally, LSP illumination sources are often constructed to collect broadband illumination only from the center of the gas containment element within the LSP illumination source. In these LSP illumination sources, increasing an illumination pump source output above a certain level does not necessarily lead to a corresponding increase in the usable broadband illumination.

LSP illumination sources often control laser wavelengths using the same power source or set of power sources to generate light for different bands and pixel sizes, and cannot individually control the relative mixing ratios of a set of wavelengths where a set of wavelengths are provided to the plasma illumination source.

Embodiments of the present disclosure are directed towards providing a higher beam quality in the ignition laser source by creating a tighter beam focus and increased intensity through an optical fiber. Additional embodiments of the present disclosure are directed towards focusing one or more laser beams into one or more cores of an optical fiber, allowing for plasma ignition at lower laser power levels. It is noted that this also allows for plasma ignition and sustaining of the plasma with reduced risk of fiber damage.

Embodiments of the present disclosure are also directed towards a set of user-selectable and individually controllable power sources to control the shape, size, and temperature of the plasma as well as the amount of power collected from different wavelength bands. Additional embodiments of the present disclosure are directed towards varying the laser wavelengths generated by the set of laser sources to mitigate the observed plasma brightness saturation and optimize the amount of collectible power. Further embodiments of the present disclosure are directed towards sustaining a plasma utilizing wavelengths of the laser beam illumination such that they do not correspond with an absorption peak of the gas medium of the LSP illumination source. Further embodiments are directed towards disabling high-absorption ignition wavelengths when sustaining the plasma.

Potential uses for the one or more embodiments of the present disclosure include, but are not limited to, driving difficult-to-ignite pumps at higher operating laser pump powers with less plasma growth and collectible power saturation, and running smaller pixel inspections during a sample inspection process.

FIG. 1A illustrates an illumination pump source 100, in accordance with one or more embodiments of the present disclosure. In one embodiment, the pump source 100 includes a set of power sources 101. For example, the set of power sources 101 may include a first power source 102a configured to generate a first laser beam 103a. By way of another example, the set of power sources 101 may include a second power source 102b configured to generate a second laser beam 103b. By way of another example, the set of power sources 101 may include a third power source 102c configured to generate a third laser beam 103c. For instance, the set of power sources 101 may include any laser source capable of emitting illumination in the range of approximately 100 nm to 1.5 μm.

In another embodiment, at least some of the power sources 102a, 102b, 102c emit laser beams 103a, 103b, 103c having different wavelengths. For example, the first power source 102a may generate a first laser beam 103a made up of light of a first wavelength $\lambda_1$ (or a first wavelength range). By way of another example, the second power source 102b may generate a second laser beam 103b made up of light of a second wavelength $\lambda_2$ (or a second wavelength range). By way of another example, the third power source 102c may generate a third laser beam 103*c* made up of light of a third wavelength $\lambda_3$ (or a third wavelength range) and so on.

It is noted herein that source 100 is not limited to three power sources as described above. Embodiments of the present disclosure may extend to N power sources for generating N laser beams made up of light of an Nth wavelength $\lambda_n$ (or an Nth wavelength range). Therefore, the above description should not be interpreted as a limitation and is provided merely for illustrative purposes.

The set of power sources 101 may include any laser system known in the art. For example, the illumination pump source 100 may include any laser system known in the art capable of emitting radiation in the infrared, visible or ultraviolet portions of the electromagnetic spectrum.

In one embodiment, the illumination pump source 100 may include one or more diode lasers. For example, the illumination pump source 100 may include one or more diode lasers. For instance, the illumination pump source may include one or more multi-kilowatt diode lasers.

It is noted herein a diode laser of illumination pump source 100 may be selected for implementation such that the wavelength of the diode laser is tuned to any absorption line of any plasma (e.g., ionic transition line) or plasma-producing gas (e.g., highly excited neutral transition line) known in the art. As such, the choice of a given diode laser (or set of diode lasers) will depend on the type of gas contained within the gas containment element.

In one embodiment, the illumination pump source 100 may include one or more continuous wave (CW) lasers. For example, the illumination pump source 100 may include one or more CW infrared laser sources. In another embodiment, the illumination pump source 100 may include one or more pulsed lasers configured to generate pulsed laser light. In another embodiment, the illumination pump source 100 may include one or more modulated lasers configured to generate modulated laser light.

In another embodiment, the illumination pump source 100 may include an ion laser. For example, the illumination pump source 100 may include any noble gas ion laser known in the art.

In another embodiment, the illumination pump source 100 may include one or more frequency converted laser systems. For example, the illumination pump source 100 may include a Nd:YAG or Nd:YLF laser having a power level exceeding 100 watts. In another embodiment, the illumination pump source 100 may include a broadband laser.

In one embodiment, the pump source 100 includes one or more optical elements. The pump source 100 may include any optical elements known in the optical arts, such as, but not limited to, steering optics, mirrors, beam splitters, collecting apertures, filters, and the like. For example, as illustrated in FIG. 1A, the pump source 100 may include, but is not limited to, a set of dichroic mirrors 104*a*, 104*b*, 104*c*.

In one embodiment, the sets of dichroic mirrors 104*a*, 104*b*, 104*c* are arranged so as to reflect and/or transmit the outputs of the multiple power sources 102*a*, 102*b*, 102*c*. For example, the first dichroic mirror 104*a* may be selected such that it is reflective of light of wavelength $\lambda_1$, so that light emitted by power source 102*a* is reflected by the first dichroic mirror 104*a* to the second dichroic mirror 104*b*. By way of another example, the second dichroic mirror 104*b* may be selected such that it is reflective of light of wavelength $\lambda_2$, but transmissive of light of wavelength $\lambda_1$. In this regard, light emitted by the power source 102*a* and 102*b* is transmitted and reflected, respectively, to the third dichroic mirror 104*c*. By way of another example, the third dichroic mirror 104*c* may be selected such that it is reflective of light of wavelength $\lambda_3$, but transmissive of one or more of light of wavelength $\lambda_1$ and light of wavelength $\lambda_2$. It is further noted herein that the embodiments of the present disclosure may extend to N dichroic mirrors for reflecting and transmitting N laser beams made up of light of an Nth wavelength $\lambda_n$ (or an Nth wavelength range). Therefore, the above description should not be interpreted as a limitation and is provided merely for illustrative purposes.

In another embodiment, the set of dichroic mirrors 104*a*, 104*b*, 104*c* are arranged so as to combine the outputs of the multiple power sources 102*a*, 102*b*, 102*c*.

It is noted herein that the source 100 is not limited to the dichroic mirror arrangement described above and illustrated in FIG. 1A, which is provided merely for illustrative purposes. For example, the source 100 may be designed in such a way that the outputs of powers sources 102*a*, 102*b*, 102*c* are only reflected by dichroic mirrors 104*a*, 104*b*, 104*c*, respectively, and are not transmitted through other dichroic mirrors (e.g., light of wavelength $\lambda_1$ is reflected by mirror 104*a*, but not transmitted by one or more of mirror 104*b* or mirror 104*c*; light of wavelength $\lambda_2$ is reflected by mirror 104*b*, but not transmitted by mirror 104*c*). It is recognized herein that illumination from the multiple sources 102*a*, 102*b*, 102*c* may be combined using any combination of optical elements known in the art.

In another embodiment, the one or more optical elements include one or more lenses 120. For example, the one or more lenses 120 may include a collecting lens. For instance, the broad diameter of the collecting lens may be greater than the thickness of the single collection lens. In another embodiment, the one or more lenses 120 are arranged so as to collect at least some of the first laser beam 103*a* of first wavelength $\lambda_1$, second laser beam 103*b* of second wavelength $\lambda_2$, and third laser beam 103*c* of third wavelength $\lambda_3$.

In another embodiment, the one or more lenses 120 are arranged so as to combine the first laser beam 103*a* (first wavelength $\lambda_1$), the second laser beam 103*b* (second wavelength $\lambda_2$), and/or the third laser beam 103*c* (third wavelength $\lambda_3$) into a pump illumination beam 122.

In another embodiment, the one or more optical elements focus or steer at least some of the pump illumination 122 into an optical fiber 130. For example, the one or more lenses 120 and the dichroic mirror 104*a* may couple light of wavelength $\lambda_1$ into a first region of the optical fiber 130. Additionally, the one or more lenses 120 and dichroic mirror 104*b* may couple light of wavelength $\lambda_2$ into a second region of the optical fiber 130. Further, the one or more lenses 120 and dichroic mirror 104*c* may couple light of the third wavelength $\lambda_3$ into a third region of the optical fiber 130.

It is noted herein the source 100 may be designed such that only the one or more lenses 120 couple a selection of light into regions of the optical fiber 130. It is further noted herein the source 100 may be designed such only the dichroic mirrors 104*a*, 104*b*, 104*c* couple a selection of light into regions of the optical fiber 130. It is further noted herein the dichroic mirrors 104*a*, 104*b*, 104*c* may instead be focusing mirrors. Here, the focusing mirrors may couple a selection of the pump illumination 122 to one or more regions of the optical fiber 130. Therefore, the above description should not be interpreted as a limitation and is provided merely for illustrative purposes.

It is further noted herein that the embodiments of the present disclosure may extend to N regions of the optical fiber 130 to which N laser beams made up of light of an Nth wavelength $\lambda_n$ (or an Nth wavelength range) may be coupled. Therefore, the above description should not be interpreted as a limitation and is provided merely for illustrative purposes.

Implementing an optical fiber within a system for generating a laser-sustained plasma is generally described in U.S. patent application Ser. No. 14/667,235, filed on Mar. 24, 2015, which is incorporated herein by reference in its entirety. Implementing an optical fiber within a system for generating a laser-sustained plasma is also generally described in PCT Patent Publication No. WO/2014/098647, filed Aug. 23, 2013; and PCT Patent Publication No. WO/2014/168519, filed Aug. 4, 2014, which are each incorporated herein by reference in their entirety.

In another embodiment, the optical fiber 130 outputs the pump illumination 122 through an end cap 131. For example, the end cap 131 may include, but is not limited to, a nozzle, aperture, lens, diffuser, filter, or any other optical element known in the art.

It is noted that one or more power sources 101 may be housed in a housing that is separate from the remainder of the power sources 101. For example, one or more power sources 101 emitting laser light with ignition may be housed separately from one or more power sources 101 emitting laser light with sustaining wavelengths.

In one embodiment, the one or more of the set of power sources are user-selectable and individually controllable. In another embodiment, the user generates one or more laser beams with different wavelengths with the set of power sources. For example, the user may generate ignition laser beams with a first power source. Here, the ignition laser beams have high-absorption wavelengths. In another embodiment, the user generates one or more sustaining laser beams with at least an additional power source once the plasma establishes a background. In another embodiment, the user directs the set of laser beams through one or more optical elements. Here, the optical elements create a pump illumination. In another embodiment, the user directs different portions of the pump illumination into different regions of an optical fiber. For example, the ignition laser beam portion of the pump illumination may be directed into one or more inner regions of the optical fiber. Additionally, the sustaining laser beam portion of the pump illumination may be directed into one or more outer regions of the optical fiber. In another embodiment, a user modifies one or more operational parameters of the set of power sources to alter the outputted pump illumination. For example, modifying one or more operational parameters of the set of power sources alters one or more of the size, shape, and temperature of a laser-sustained plasma. It is noted that altering the outputted pump illumination may result in a high beam quality, which can minimize plasma brightness saturation and optimize collectible power output.

In another embodiment, the user individually addresses any of the set of power sources, adjusting one or more operational parameters of the set of power sources to alter the quality of the pump illumination. For example, the user may enable or disable one or more generated laser beams. By way of another example, a user may switch between any of the set of power sources. For instance, a user may turn off one or more power sources used for igniting the plasma and simultaneously turn on one or more power sources used for sustaining (high-power operation) the plasma. By way of another example, a user may adjust a laser beam wavelength in real-time without turning off the laser beam entirely, allowing a plasma to stay ignited during the adjustment process. For instance, the user may reduce the power of a generated laser beam. Additionally, the user may reduce the power of the set of ignition laser beams when switching to sustaining mode. By way of another example, the user may adjust one or more wavelength bands of the set of laser beams. By way of another example, the user may change the relative mixing ratios of the set of laser beams within the pump illumination.

In another embodiment, the user individually addresses any of the one or more optical elements in the system to alter the quality of the pump illumination. For example, a user may adjust one or more optical elements to focus or steer a portion of the pump illumination to a different region of the optical fiber. By way of another example, the user may alter the spatial content of a portion of the pump illumination in a single-core fiber including, but not limited to, a multiple-step index fiber with multiple refractive indices. By way of another example, the user may alter the focus location of a portion of the pump illumination in a multi-core fiber.

In another embodiment, the illumination pump source is connected to a controller. In this embodiment, the controller includes firmware or software designed to adjust the wavelength and level of output for one or more generated laser beams in response to one or more inputs from a user, either automatically or in response to feedback from the user. For example, upon receipt of an application selection for the pump illumination source, the controller may generate more ignition laser beams and couple them to the optical fiber via the one or more optical elements. By way of another example, the controller may generate one or more sustaining laser beams and couple them to the optical fiber via the one or more optical elements. By way of another example, the controller may create a pump illumination from the set of laser beams. By way of another example, the controller may adjust the pump illumination to mitigate plasma brightness saturation and optimize the collectible power from a laser-sustained plasma illumination. For instance, the controller may adjust the output levels in response to prompts from the user. Additionally, the controller may adjust the pump illumination in response to information received from a light-sustained plasma illumination system, described in detail further herein, by following one or more program instructions stored within the controller.

Figure 1B:
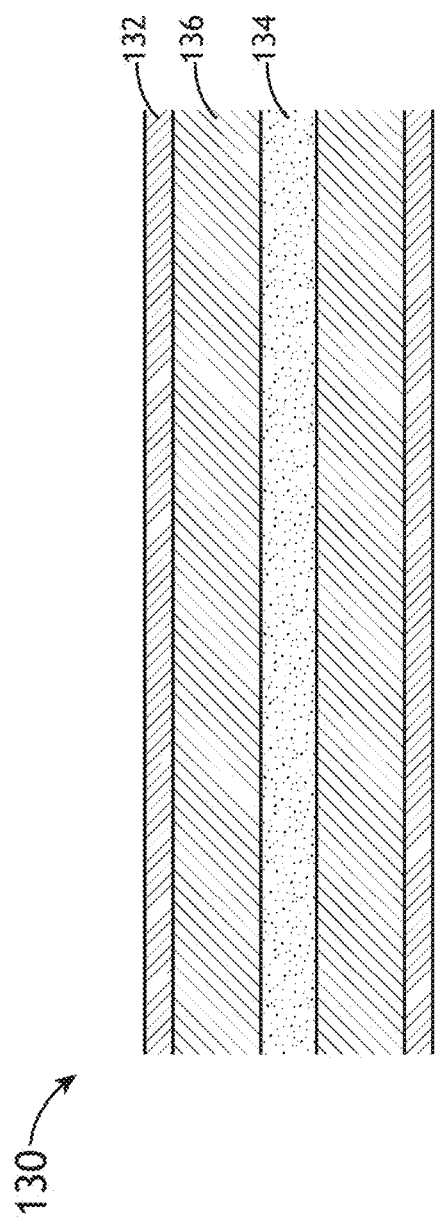
FIG. 1B illustrates an optical fiber, in accordance with one or more embodiments of the present disclosure.
Figure 1C:
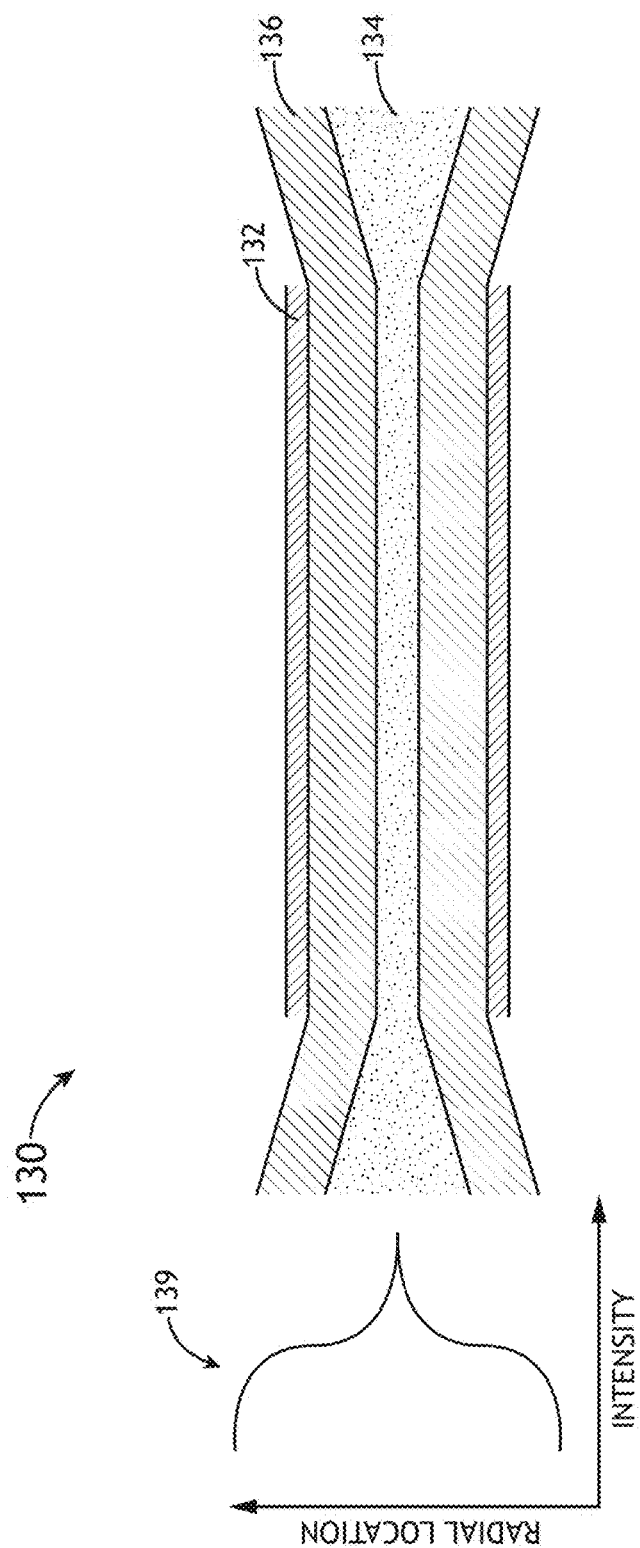
FIG. 1C illustrates an optical fiber, in accordance with one or more embodiments of the present disclosure.

In one embodiment, as illustrated in FIGS. 1B and 1C, the optical fiber 130 is a multiple-step index fiber. For example, the multiple-step index fiber has multiple fiber layers, where each fiber layer has a different refractive index. In another embodiment, the optical fiber 130 includes a cladding layer 132 surrounding the multiple fiber layers. In another embodiment, the one or more optical elements couple one or more ignition laser beams into a first index fiber portion of the multiple-step index fiber, while coupling one or more sustaining beams into a second index fiber portion of the multiple-step index fiber. For example, the one or more optical elements couple one or more ignition laser beams into a first index fiber portion, where the first index fiber portion includes one or more inner steps 134. By way of another example, the one or more optical elements couple one or more sustaining laser beams into a second index fiber portion, where the second index fiber portion includes one or more outer steps 136. By way of another example, the one or more optical elements couple one or more sustaining laser beams into the first index fiber portion, where the first index fiber portion includes one or more inner steps 134, following the completion of plasma ignition.

It is noted the spatial coupling of the one or more ignition laser beams within the one or more inner steps 134 of the optical fiber 130 results in a higher degree of focus of the pump illumination 122 to a plasma. As illustrated by graph 139, a tight spatial coupling of the ignition laser beams increases the power intensity at the center of the optical fiber 130, which allows for ignition of the plasma at lower power levels.

It is further noted the one or more ignition laser beams may have lower beam powers, and the one or more sustaining laser beams may have higher beam powers.

Figure 1D:
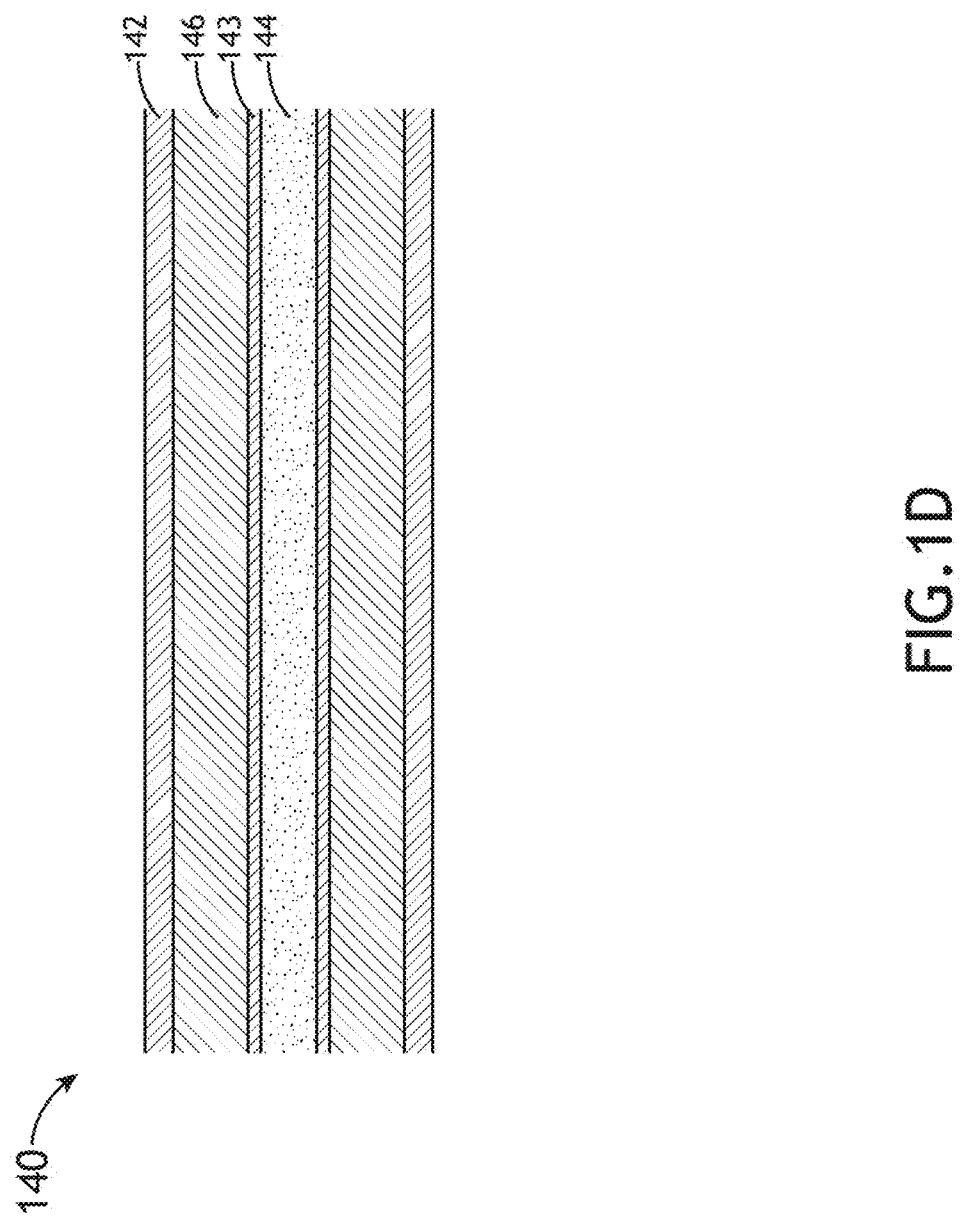
FIG. 1D illustrates an optical fiber, in accordance with one or more embodiments of the present disclosure.

FIG. 1D illustrates an optical fiber 140, in accordance with one or more embodiments of the present disclosure. In one embodiment, the optical fiber 140 is a multi-core optical fiber including one or more cores. In another embodiment, the optical fiber 140 includes a cladding layer 142 surrounding the one or more cores of the multi-core optical fiber 140. In another embodiment, one or more of the multiple cores are surrounded by a cladding layer 143. In this regard, the cladding layer 143 separates select cores from the other cores of the optical fiber 140. In another embodiment, the one or more optical elements couple one or more ignition laser beams into one or more first cores of the multi-core optical fiber 140, while coupling one or more sustaining beams into one or more second cores of the multi-step optical fiber 140. For example, the one or more optical elements couple one or more ignition laser beams into a first core, where the first core includes an inner core 144. By way of another example, the one or more optical elements couple one or more sustaining laser beams into a second core, where the second core includes an outer core 146. By way of another example, the one or more optical elements couple one or more sustaining laser beams into the first core, where the first core includes an inner core 144, following the completion of plasma ignition.

It is noted a more tightly focused geometry of the one or more ignition laser beams within the one or more inner cores 144 results in a higher degree of focus of the pump illumination 122 to a plasma. It is further noted that a multi-core fiber may include cores with different numerical aperture (NA) values or refractive indices. For example, the one or more inner cores 144 may have different numerical aperture (NA) values than the one or more outer cores 146 to prevent back reflection.

Referring generally to FIGS. 2A-3B, the provided graphical data illustrates that a more tightly focused geometry improves the ignition process alongside the use of high-absorption laser wavelengths, whether via focused spatial coupling in a single-core fiber or via a multi-core fiber.

FIGS. 2A and 2B illustrate a 1 kW beam pumping through a single-core fiber. FIG. 2A illustrates a graph 200 of the power density of a beam pumped through a 2000 μm single-core fiber, with a high power density region 202. For comparison, FIG. 2B illustrates a graph 210 of the power density of a beam pumped through a 600 μm single-core fiber, with a high power density region 212.

FIGS. 3A and 3B illustrate a 1 kW beam pumping through a 2000 μm multi-core fiber. FIG. 3A illustrates a graph 300 of the power density of a beam with wavelengths 1044 nm and 1066 nm pumping through a 2000 μm fiber, with a high power density region 302, where the inner 300 μm is obscured by a separate inner fiber core. For comparison, FIG. 3B illustrates a graph 310 of the power density of a beam with a wavelength 965 nm through only the inner fiber core, with a high power density region 312.

Based on these simulations, it is noted that a smaller overall optical fiber diameter may result in an increased power density. Additionally, it is further noted that a smaller overall optical fiber diameter may result in a tighter spread of power density.

Figure 1E:
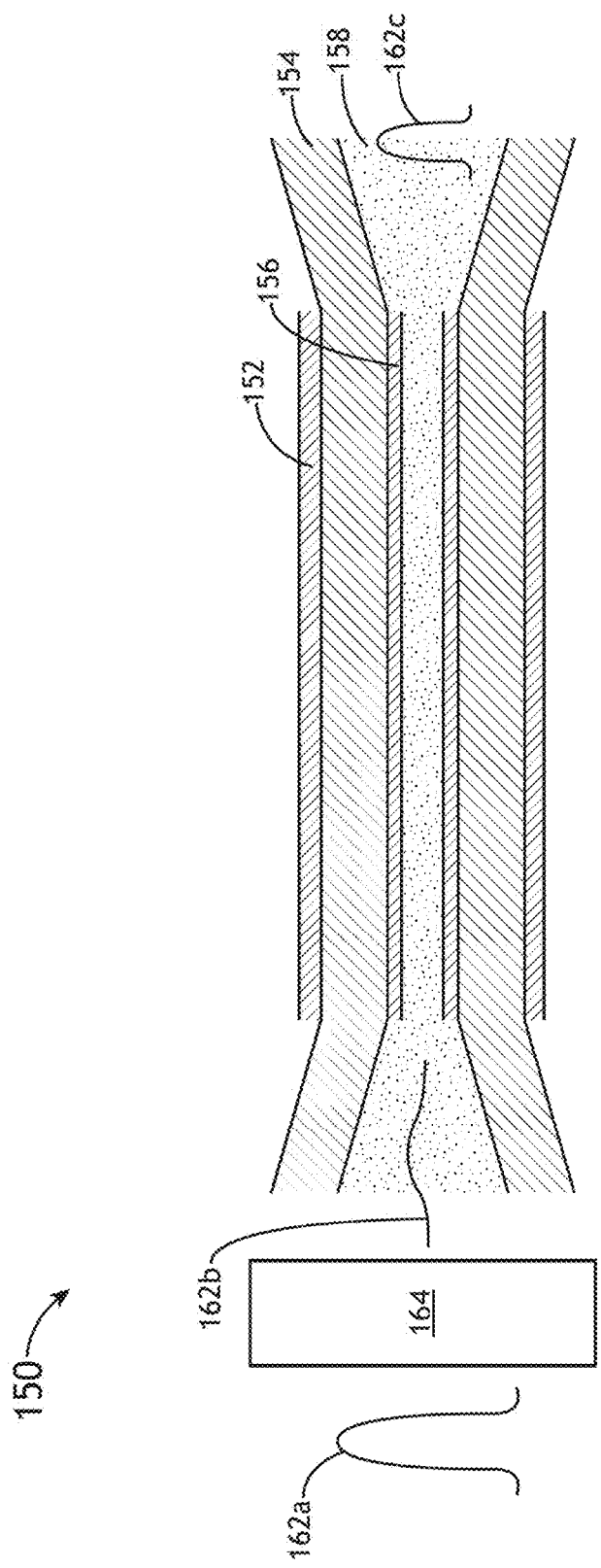
FIG. 1E illustrates an optical fiber, in accordance with one or more embodiments of the present disclosure.

FIG. 1E illustrates an optical fiber 150 for use with a continuous wave (CW) or pulsed laser, in accordance with one or more embodiments of the present disclosure. In one embodiment, the optical fiber 150 is a multi-core optical fiber including one or more cores. In another embodiment, the optical fiber 150 includes a cladding layer 152 surrounding the one or more cores of the multi-core optical fiber 150. In another embodiment, one or more of the multiple cores are surrounded by a cladding layer 156. In this regard, the cladding layer 156 separates one or more selected cores from the other cores of the optical fiber 150. In another embodiment, the one or more optical elements couple one or more ignition laser beams into one or more first cores of the multi-core optical fiber 150, while coupling one or more sustaining beams into one or more second cores of the multi-step optical fiber 150. For example, the one or more optical elements couple one or more ignition laser beams into a first core, where the first core includes one or more inner cores 158. By way of another example, the one or more optical elements couple one or more sustaining laser beams into a second core, where the second core includes one or more outer cores 154. By way of another example, the one or more optical elements couple one or more sustaining laser beams into the one or more first cores, where the one or more first cores include one or more inner cores 158, following the completion of plasma ignition.

In another embodiment, a CW laser or pulsed laser 162a is focused towards and coupled to the one or more inner cores 158. In another embodiment, the laser beam 162a is passed through a pulse stretcher 164, becoming a stretched laser beam 162b. For example, use of the pulse stretcher 164 may produce negative dispersion within the one or more inner cores 160 of the optical fiber 150. By way of another example, negative dispersion may compress the laser beam 162b, giving it a shorter pulse duration. By way of another example, the negative dispersion may create a compressed laser beam 162c from the stretched laser beam 162b, where the compressed laser beam 162c is used to ignite the plasma. It is noted herein a pulse stretcher may alternatively or in addition be implemented on laser beams coupled to the one or more outer cores 154.

It is noted a set of CW lasers or pulsed lasers may be coupled to at least one of the one or more outer cores 154 and the one or more inner cores 158 of the optical fiber 150. Coupling to multiple cores may assist in the alignment of laser beams. Coupling to multiple cores may be also necessary for combined CW laser/pulsed operation applications. Combining CW lasers and pulsed lasers into multiple cores of the same multi-core fiber may remove cost, complexity, and potential safety risks of a high-voltage-arc gas breakdown required for plasma ignition.

It is further noted a CW laser may be in place of or in addition to other ignition laser beams. It is further noted that, depending on the initial pulse duration and the damage threshold of the optical fiber, stretching of the pulse may not be necessary. In this instance, a pulse stretcher 164 may not be required.

Figure 4A:
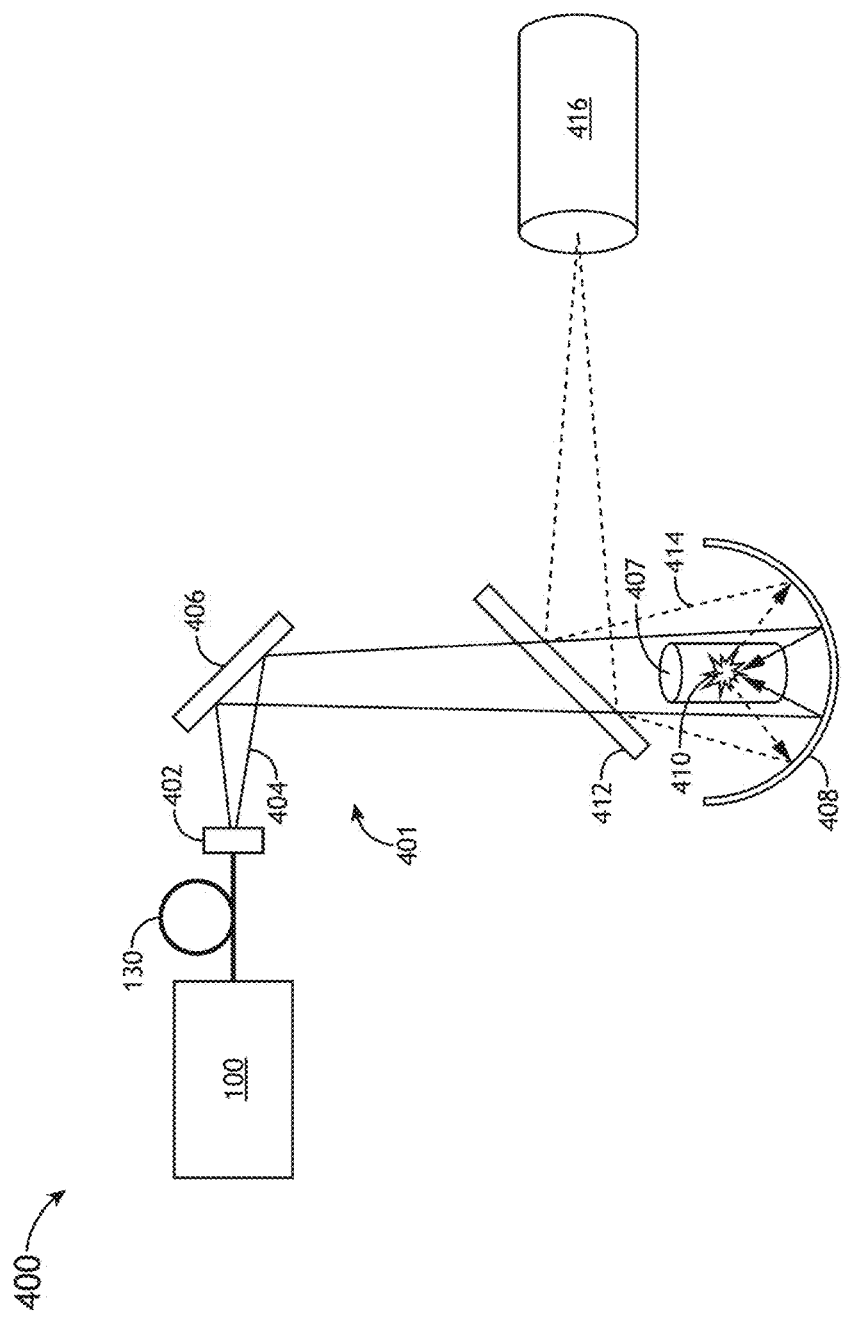
FIG. 4A illustrates a system for imaging a sample with laser-sustained plasma illumination, in accordance with one or more embodiments of the present disclosure.
Figure 4B:
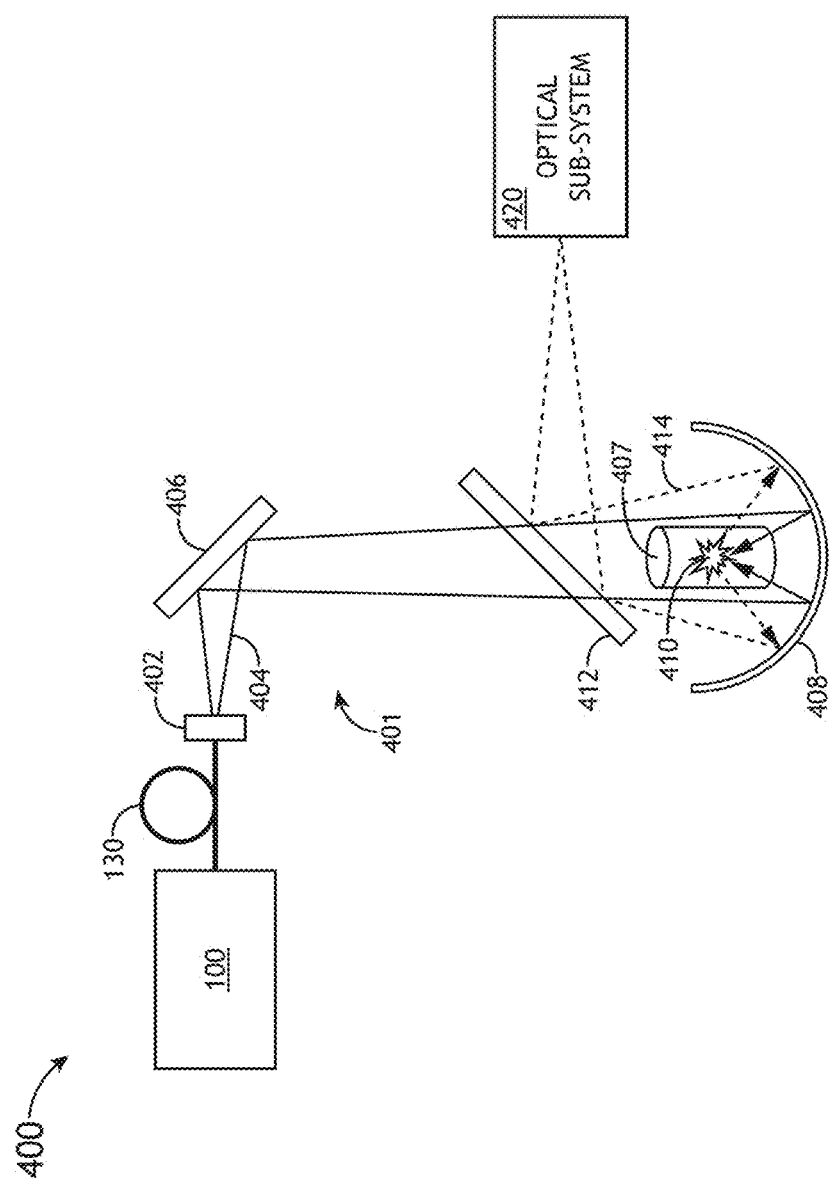
FIG. 4B illustrates a system for imaging a sample with laser-sustained plasma illumination, in accordance with one or more embodiments of the present disclosure.

FIGS. 4A and 4B illustrate an optical system 400 implementing the illumination pump source 100, in accordance with one or more embodiments of the present disclosure. It is noted herein the embodiments and examples described throughout the present disclosure should be interpreted to extend to system 400 unless otherwise noted. It is noted herein the system 400 should be interpreted to extend to any plasma-based light source known in the art.

In one embodiment, the system 400 includes a laser-sustained plasma (LSP) illumination subsystem 401. It is noted herein that the terms 'LSP illumination subsystem' and 'broadband illumination source sub-system' are used interchangeably with 'LSP illuminator' throughout the present disclosure. In one embodiment, the LSP illuminator 401 includes the illumination pump source 100. In another embodiment, the illumination pump source 100 outputs pump illumination 404 through the optical fiber 130. In another embodiment, the pump illumination 404 includes multiple laser light components with different wavelengths, as discussed previously herein. For example, the pump illumination 404 may include, but is not limited to, infrared (IR) radiation, visible light and/or ultraviolet light. By way of another example, the pump illumination 404 may include, but is not limited to, continuous wave (CW) radiation and/or pulsed radiation. In another embodiment, the optical fiber 130 outputs the pump illumination 404 through an end cap 402. For example, the end cap 402 may include, but is not limited to, a nozzle, aperture, lens, diffuser, filter, and any other optical element known in the art.

In one embodiment, the LSP illuminator 401 includes a containment element 407. In another embodiment, the gas containment element 407 contains a volume of gas used to establish and maintain a plasma 410. For example, as shown in FIG. 4A, the gas containment element 407 may include, but is not limited to, a plasma cell. It is noted herein that the scope of the present disclosure is not limited to an LSP illuminator with a plasma cell, which is provided merely for illustrative purposes. Rather, the gas containment element 407 may include any gas containment element known in the art of laser sustained plasma sources, such as, but not limited to, a plasma bulb, a plasma cell, or a plasma chamber. The use of a plasma chamber and a plasma cell is generally described in U.S. patent application Ser. No. 14/459,155, filed Aug. 13, 2014. The use of a plasma bulb is generally described in U.S. patent application Ser. No. 14/699,781, filed Apr. 29, 2015, which are incorporated herein by reference in their entirety.

In some embodiments, the transmitting portion of the gas containment element 407 (e.g., chamber, cell or bulb) may be formed from any material known in the art that is at least partially transparent to radiation 414 generated by plasma 410 and/or the pump illumination 404. In one embodiment, the transmitting portion of the gas containment element 407 may be formed from any material known in the art that is at least partially transparent to EUV radiation, VUV radiation, DUV radiation, UV radiation and/or visible light generated by the plasma 410. In another embodiment, the transmitting portion of the gas containment element 407 may be formed from any material known in the art that is at least partially transparent to IR radiation, visible light and/or UV light from the illumination pump source 100.

In one embodiment, the gas containment element 407 may contain any selected gas (e.g., argon, xenon, mercury or the like) known in the art suitable for generating a plasma upon absorption of pump illumination 404. In one embodiment, focusing illumination 404 from the illumination pump source 100 into the volume of gas causes energy to be absorbed by the gas or plasma (e.g., through one or more selected absorption lines) within the gas containment element 407, thereby "pumping" the gas species in order to generate and/or sustain a plasma. In another embodiment, although not illustrated, the gas containment element 407 may include a set of electrodes for initiating the plasma 410 within the internal volume of the gas containment element 407, whereby the illumination from the illumination pump source 100 maintains the plasma 410 after ignition by the electrodes.

It is contemplated herein that the system 400 may be utilized to initiate and/or sustain a plasma 410 in a variety of gas environments. In one embodiment, the gas used to initiate and/or maintain plasma 410 may include a noble gas, an inert gas (e.g., noble gas or non-noble gas) or a non-inert gas (e.g., mercury). For example, the selected gas environment may include Xe. In another embodiment, the gas used to initiate and/or maintain a plasma 410 may include a mixture of two or more gases (e.g., mixture of inert gases, mixture of inert gas with non-inert gas or a mixture of non-inert gases). In another embodiment, the gas may include a mixture of a noble gas and one or more trace materials (e.g., metal halides, transition metals and the like). For example, the selected gas may include HgXe.

It is noted that the embodiments of the present disclosure may be extended to a number of gases. For example, gases suitable for implementation in the embodiments of the present disclosure may include, but are not limited to, Xe, Ar, Ne, Kr, He, $N_2$, $H_2O$, $O_2$, $H_2$, $D_2$, $F_2$, $CH_4$, one or more metal halides, a halogen, Hg, Cd, Zn, Sn, Ga, Fe, Li, Na, Ar:Xe, ArHg, KrHg, XeHg, and the like. It is noted herein the embodiments of the present disclosure should be interpreted to extend to any light pumped plasma generating system and should further be interpreted to extend to any type of gas suitable for sustaining a plasma 410 within a gas containment element 407, such as a gas chamber, a plasma cell, or a plasma bulb.

By way of example, the volume of gas used to generate a plasma 410 may include argon. For instance, the gas may include a substantially pure argon gas held at pressure in excess of 5 atm (e.g., 20-50 atm). It is noted that in the case of an argon-based plasma, the illumination pump source 100 used to pump argon ions may include an Ar+ laser. In another instance, the gas may include a substantially pure krypton gas held at pressure in excess of 5 atm (e.g., 20-50 atm). In another instance, the gas may include a mixture of argon gas with an additional gas.

It is noted that where the gas within the gas containment element 407 is or includes argon, the illumination pump source 100 may include a CW laser (e.g., fiber laser or disc Yb laser) configured to emit radiation at 1069 nm. It is noted that this wavelength fits to a 1068 nm absorption line in argon and as such is particularly useful for pumping argon gas. It is noted herein that the above description of a CW laser is not limiting and any laser known in the art may be implemented in the context of the embodiments of the present disclosure.

In another embodiment, the pump illumination 404 is directed into the gas containment element 407 along a pump path by one or more illumination optical elements to one or more focal spots within the volume of gas in the gas containment element 407 by any manner known in the art. For example, the pump illumination 404 may be reflected by a mirror 406 towards the gas containment element 407 from the optical fiber 130. By way of another example, the pump illumination 404 may be directed directly into the gas containment element 407 by the optical fiber 130. For instance, the optical fiber 130 may be coupled to the exterior of the gas containment element 407. Additionally, the optical fiber 130 may be coupled to the interior of the gas containment element 407. Where the optical fiber 130 is a multi-core optical fiber, one or more of the optical fiber 130 cores may be coupled individually to the gas containment element 407. By way of another example, at least a portion of the optical fiber 130 may be coupled directly to the gas containment element 407 and at least a portion of the pump illumination 404 is reflected by a mirror 406 towards the gas containment element 407. By way of another example, the pump illumination 404 may be focused into the gas containment element 407 via one or more focusing lenses.

In another embodiment, the pump illumination 404 is focused into the volume of gas contained within the gas containment element 407 by any manner known in the art. For example, the LSP illuminator 401 may include a collector 408, or reflector, configured to focus (e.g., via a reflective internal surface) the pump illumination 404 from the illumination pump source 100 into the volume of gas contained within the gas containment element 407 to ignite/sustain the plasma 410.

The collector 408 may take on any physical configuration known in the art suitable for focusing illumination emanating from the illumination pump source 100 into the volume of gas contained within the gas containment element 407. In one embodiment, the collector 408 may include a concave region with a reflective internal surface suitable for receiving illumination 404 from the illumination pump source 100 and focusing the illumination into the volume of gas contained within the gas containment element 407. For example, the collector 408 may include an ellipsoid-shaped collector having a reflective internal surface.

It is noted that the scope of the present disclosure is not limited to the collector 408 described above and depicted in FIG. 4A to focus pump illumination 404 into the gas containment element 407, which is provided merely for illustrative purposes. Rather, any mechanism known in the art may be implemented to focus pump illumination into the gas containment element 407. For example, an optical recycling system may be implemented when igniting and sustaining the plasma 410. For instance, one or more recycler optical elements may reflect unused pump illumination 404 back into the volume of gas contained within the gas containment element 407 and/or towards the plasma 410 for increased output of broadband illumination 414. The use of an optical recycling system is generally described in U.S. patent application Ser. No. 15/187,590, filed Jun. 20, 2016, which is incorporated herein by reference in its entirety.

In another embodiment, the plasma 410 emits broadband illumination 414 including one or more second selected wavelengths, such as, but not limited to, EUV radiation, VUV radiation, DUV radiation, UV radiation, and/or visible light. For example, the LSP illuminator 401 may include, but is not limited to, any LSP configuration capable of emitting light having a wavelength in the range of 100 nm to 1.5 μm. By way of another example, the LSP illuminator 401 may include, but is not limited to, any LSP configuration capable of emitting light having a wavelength below 100 nm.

In another embodiment, the broadband illumination 414 may be collected by one or more collection optical elements along a collection path in any manner known in the art. For example, the collector 408 is arranged to collect the broadband illumination 414 (e.g., VUV radiation, DUV radiation, UV radiation, EUV radiation, and/or visible light) emitted by plasma 410 and direct the broadband illumination 414 to one or more additional optical elements (e.g., steering optics, a mirror, a beam splitter, a collecting aperture, a filter, a homogenizer and the like). For instance, the collector 408 may collect EUV broadband radiation, VUV broadband radiation, DUV broadband radiation, UV broadband radiation, and/or visible light emitted by plasma 410 and direct the broadband illumination 414 to a dichroic mirror 412 (e.g., cold mirror).

In another embodiment, as shown in FIG. 4A, the cold mirror 412 may optically couple the LSP illuminator 401 to a homogenizer 416. In another embodiment, as shown in FIG. 4B, the cold mirror 412 (or any other optical device) may optically couple the LSP illuminator 401 to an optical input of an optical sub-system 420. For example, the optical sub-system 420 may include, but is not limited to, an inspection tool, a metrology tool, or a lithography tool. In this regard, the LSP illuminator 401 may deliver EUV radiation, VUV radiation, DUV radiation, UV radiation, and/or visible radiation to downstream optical elements of any optical sub-system 420 known in the art, such as, but not limited to, an inspection tool or a metrology tool.

It is noted that the scope of the present disclosure is not limited to the collector 408 described above and depicted in FIG. 4A to collect broadband illumination 414 from the gas containment element 407, which is provided merely for illustrative purposes. Rather, any mechanism known in the art may be implemented to collect broadband illumination 414 from the gas containment element 407. For example, the LSP illuminator 401 may include any number and type of additional optical elements. For instance, the set of additional optics may include collection optics configured to collect broadband illumination 414 emanating from the plasma 410. Additionally, the LSP illuminator 401 may include one or more additional optical elements arranged to direct illumination from the collector 408 to downstream optics. Further, the set of additional optics may include one or more filters placed along either the illumination pathway or the collection pathway of the LSP illuminator 401 in order to filter illumination prior to light entering the gas containment element 407 or to filter illumination following emission of the light from the plasma 410. By way of another example, an optical recycling system may be implemented when collecting the broadband illumination 414. For example, the one or more recycler optical elements may reflect un-collected broadband illumination 414 towards any of the cold mirror 412, the homogenizer 416, and the imaging sub-system 420. The use of an optical recycling system is generally described in U.S. patent application Ser. No. 15/187,590, filed Jun. 20, 2016, which is incorporated herein by reference in its entirety.

In additional embodiments, the optical sub-system 420 includes an illumination sub-system. For example, the illumination sub-system may include any number of optical elements to deliver the broadband illumination 414 to the surface of one or more samples such as, but not limited to, steering optics, mirrors, beam splitters, collecting apertures, filters, homogenizers and the like. By way of another example, the illumination sub-system includes a sample stage for securing the one or more samples.

In additional embodiments, the optical sub-system 420 includes a detector sub-system suitable for performing inspection of a sample. In one embodiment, the detector sub-system includes a detector. For example, the detector of the detector sub-system may include any appropriate detector known in the art. For instance, the detector may include, but is not limited to, a CCD detector, a CCD-TDI detector and the like. In addition, the output of the detector may be communicatively coupled to a controller. In another embodiment, the detector sub-system includes an objective. For example, the objective may be configured to collect illumination from a surface of the sample and focus the collected illumination via a collection pathway to the detector to form an image of at least a portion of the surface of the one or more samples. In another embodiment, the detector sub-system includes an optical recycler sub-system.

In an additional embodiment, the optical sub-system 420 includes an optical tool characterization sub-system optically coupled to an output of the broadband illumination source sub-system.

Figure 5:
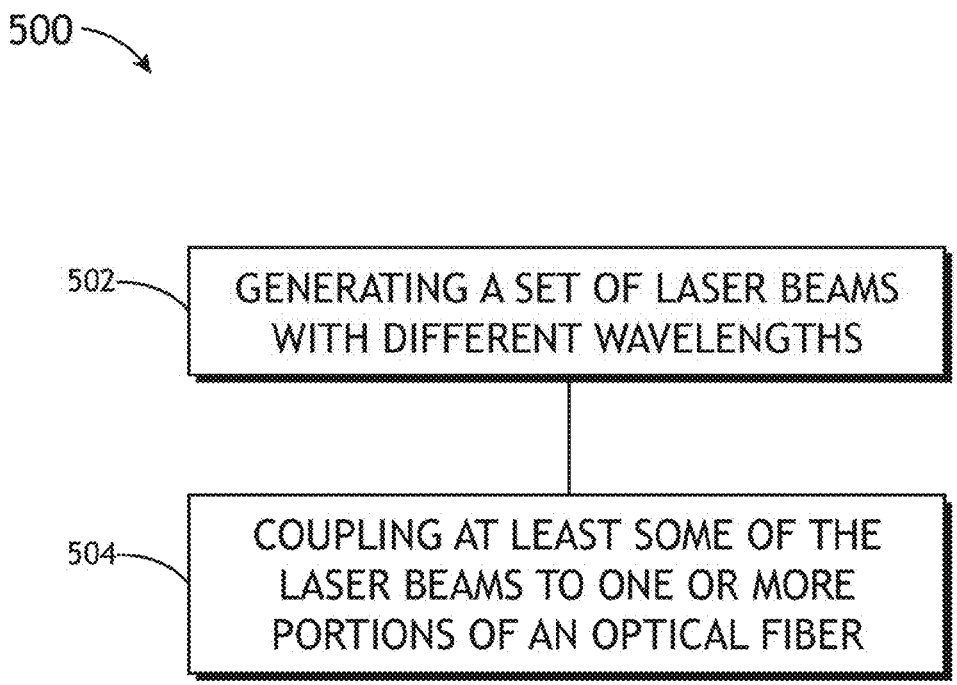
FIG. 5 illustrates a process flow diagram depicting a method for illuminating a laser-sustained plasma, in accordance with one or more embodiments of the present disclosure.

FIG. 5 illustrates a method 500 for igniting and sustaining a plasma, in accordance with the one or more embodiments of the present disclosure. In a step 502, a set of laser beams with different wavelengths are generated. In one embodiment, the set of laser beams are generated by a set of power sources. In another embodiment, one or more of the set of laser beams is optimized for igniting a plasma. In another embodiment, one or more of the set of laser beams is optimized for sustaining a plasma.

In a step 504, at least some of the laser beams are coupled to one or more portions, or regions, of an optical fiber. In one embodiment, at least some of the laser beams are coupled to one or more regions of an optical fiber via one or more optical elements.

In an additional step, one or more operational parameters of the set of power sources are adjusted. In one embodiment, the set of power sources are controllable via adjustment of the one or more operational parameters. In another embodiment, adjusting the one or more operational parameters of the set of power sources adjusts at least one of plasma size, plasma shape, or plasma temperature.

Although particular embodiments of this invention have been illustrated, it is apparent that various modifications and embodiments of the invention may be made by those skilled in the art without departing from the scope and spirit of the foregoing disclosure. Accordingly, the scope of the invention should be limited only by the claims appended hereto.

What is claimed:

1. An illumination pump source comprising:
    a first laser source configured to emit a first laser beam including illumination of a first wavelength for igniting a plasma;
    at least a second laser source configured to emit at least a second laser beam including illumination of at least a second wavelength for sustaining an ignited plasma, wherein the first wavelength is different from the at least the second wavelength;
    an optical fiber including a first region and at least a second region, wherein the optical fiber is configured to deliver the illumination emitted from the first laser source and the illumination emitted from the at least the second laser source to a plasma for generation of broadband illumination by the plasma; and
    one or more optical elements, wherein the one or more optical elements couple the first laser beam to the first region of the optical fiber, wherein the one or more optical elements couple the at least the second laser beam to the at least the second region of the optical fiber,
    wherein one or more of the first laser source or the at least the second laser source are individually controllable via one or more user-selectable operation parameters.

2. The illumination pump source in claim 1, wherein the one or more optical elements include:
    a first dichroic mirror;
    at least one additional dichroic mirror; and
    one or more lenses.

3. The illumination pump source in claim 1, wherein the optical fiber is a multiple-step index fiber, wherein the first region of the optical fiber includes an inner step of the multiple-step index fiber, wherein the at least the second region of the optical fiber includes at least one outer step of the multiple-step index fiber.

4. The illumination pump source in claim 3, wherein the one or more optical elements are configured to couple the first laser beam including illumination of the first wavelength to the inner step of the multiple-step index fiber.

5. The illumination pump source in claim 3, wherein the one or more optical elements are configured to couple the at least the second laser beam including illumination of the at least the second wavelength to the at least one outer step of the multiple-step index fiber.

6. The illumination pump source in claim 1, wherein the optical fiber includes at least two cores.

7. The illumination pump source in claim 6, wherein the optical fiber includes an inner core and at least one outer core, wherein the first region of the optical fiber includes the inner core, wherein the at least the second region of the optical fiber includes the at least one outer core.

8. The illumination pump source in claim 7, wherein the one or more optical elements are configured to couple the first laser beam including illumination of the first wavelength to the inner core.

9. The illumination pump source in claim 7, wherein the one or more optical elements are configured to couple the at least the second laser beam including illumination of the at least the second wavelength to the at least one outer core.

10. The illumination pump source in claim 1, wherein one or more of the first laser source or the at least the second laser source comprise:
    at least one of a diode laser, a continuous wave (CW) laser, or a broadband laser.

11. The illumination pump source in claim 1, wherein one or more of the first laser source or the at least the second laser source comprise:
    at least one of an infrared laser, a visible laser, or an ultraviolet laser.

12. The illumination pump source in claim 1, further comprising:
    a laser pulse stretcher.

13. The illumination pump source in claim 1, wherein adjustment of the one or more operational parameters of one or more of the first laser source or the at least the second laser source following ignition of a plasma adjusts at least one of power output or wavelength of the first laser beam or the at least the second laser beam.

14. The illumination pump source in claim 1, wherein adjustment of the one or more operational parameters of one or more of the first laser source or the at least the second laser source following the ignition of the plasma adjusts at least one of the ignited plasma size, the ignited plasma shape, or the ignited plasma temperature.

15. The illumination pump source in claim 1, wherein the one or more optical elements are individually adjustable, wherein adjusting the one or more optical elements adjusts at least one of the coupling of the first laser beam to the first region of the optical fiber or the coupling of the at least the second laser beam to the at least the second region of the optical fiber.

16. The illumination pump source in claim 1, wherein the one or more optical elements are individually adjustable, wherein the first laser beam and the at least the second laser beam are mixable within a region of the optical fiber, wherein adjusting the one or more optical elements or the one or more operational parameters adjusts at least one relative mixing ratio of the first laser beam and the at least the second laser beam within the region of the optical fiber.

17. A method for igniting and sustaining a plasma, comprising:

generating a first laser beam including illumination of a first wavelength for igniting a plasma with a first laser source and at least a second laser beam including illumination of at least a second wavelength for sustaining an ignited plasma with at least a second laser source, wherein the first wavelength is different from the at least the second wavelength, wherein one or more of the first laser source or the at least the second laser source are individually controllable via one or more user-selectable operation parameters;

coupling, via one or more optical elements, the first laser beam to a first region of an optical fiber and the at least the second laser beam to at least a second region of the optical fiber, wherein the optical fiber is configured to deliver the illumination emitted from the first laser source and the illumination emitted from the at least the second laser source to a plasma for generation of broadband illumination by the plasma; and adjusting the one or more operational parameters of one or more of the first laser source or the at least the second laser source following ignition of a plasma.

18. The method in claim 17, wherein the adjusting the one or more operational parameters of one or more of the first laser source or the at least the second laser source following the ignition of the plasma comprises:

adjusting at least one of the ignited plasma size, the ignited plasma shape, or the ignited plasma temperature via adjustment of one or more of the first laser source or the at least the second laser source.

19. The method in claim 17, wherein the adjusting the one or more operational parameters of one or more of the first laser source or the at least the second laser source following the ignition of the plasma comprises:

adjusting at least one of power output or wavelength of one or more of the first laser source or the at least the second laser source.

20. The method in claim 17, wherein the one or more optical elements are individually adjustable, wherein adjusting the one or more optical elements adjusts at least one of the coupling of the first laser beam to the first region of the optical fiber or the coupling of the at least the second laser beam to the at least the second region of the optical fiber.

21. The method in claim 17, wherein the one or more optical elements are individually adjustable, wherein the first laser beam and the at least the second laser beam are mixable within a region of the optical fiber, wherein adjusting the one or more optical elements or the one or more operational parameters adjusts at least one relative mixing ratio of the first laser beam and the at least the second laser beam within the region of the optical fiber.

22. A system for imaging a sample with a laser-sustained plasma illumination, comprising:

an illumination pump source subsystem for igniting and sustaining a plasma including:
 a first laser source configured to emit a first laser beam including illumination of a first wavelength for igniting a plasma;
 at least a second laser source configured to emit at least a second laser beam including illumination of at least a second wavelength for sustaining an ignited plasma, wherein the first wavelength is different from the at least the second wavelength;
 an optical fiber including a first region and at least a second region; and
 one or more optical elements, wherein the one or more optical elements couple the first laser beam to the first region of the optical fiber, wherein the one or more optical elements couple the at least the second laser beam to the at least the second region of the optical fiber,
 wherein one or more of the first laser source or the at least the second laser source are individually controllable via one or more user-selectable operation parameters;

a broadband illumination source subsystem, wherein the optical fiber is configured to deliver the illumination emitted from the first laser source and the illumination emitted from the at least the second laser source to the broadband illumination source subsystem, wherein the broadband illumination source subsystem comprises:
 one or more illumination optical elements configured to direct at least a portion of a pump illumination formed from the first laser beam and the at least the second laser beam;
 a gas containment element for containing a volume of gas, wherein the one or more illumination optical elements are configured to sustain a plasma within a volume of gas in the gas containment element by directing at least a portion of the pump illumination along a pump path to one or more focal spots within the volume of gas; and
 one or more collection optical elements configured to collect broadband illumination emitted by the plasma along a collection path;

a sample stage for securing one or more samples; and
an imaging subsystem including:
 a detector; and
 an objective, wherein the objective is configured to collect illumination from a surface of the sample and focus the collected illumination via a collection pathway to the detector to form an image of at least a portion of the surface of the one or more samples.

23. The system of claim 22, wherein the one or more optical elements include:
 a first dichroic mirror;
 at least one additional dichroic mirror; and
 one or more lenses.

24. The system of claim 22, wherein the optical fiber is a multiple-step index fiber, wherein the first region of the optical fiber includes an inner step of the multiple-step index fiber, wherein the at least the second region of the optical fiber includes at least one outer step of the multiple-step index fiber.

25. The system of claim 24, wherein the one or more optical elements are configured to couple the first laser beam including illumination of the first wavelength to the inner step of the multiple-step index fiber.

26. The system of claim 24, wherein the one or more optical elements are configured to couple the at least the second laser beam including illumination of the at least the second wavelength to the at least one outer step of the multiple-step index fiber.

27. The system of claim 22, wherein the optical fiber includes at least two cores.

28. The system of claim 27, wherein the optical fiber includes an inner core and at least one outer core, wherein the first region of the optical fiber includes the inner core, wherein the at least the second region of the optical fiber includes the at least one outer core.

29. The system of claim 28, wherein the one or more optical elements are configured to couple the first laser beam including illumination of the first wavelength to the inner core.

30. The system of claim 28, wherein the one or more optical elements are configured to couple the at least the second laser beam including illumination of the at least the second wavelength to the at least one outer core.

31. The system of claim 22, wherein one or more of the first laser source or the at least the second laser source comprise:
at least one of a diode laser, a continuous wave (CW) laser, or a broadband laser.

32. The system of claim 22, wherein one or more of the first laser source or the at least the second laser source comprise:
at least one of an infrared laser, a visible laser, or an ultraviolet laser.

33. The system of claim 22, further comprising:
a laser pulse stretcher.

34. The system of claim 22, wherein adjustment of the one or more operational parameters of one or more of the first laser source or the at least the second laser source following ignition of a plasma adjusts at least one of power output or wavelength of the first laser beam or the at least the second laser beam.

35. The system of claim 22, wherein adjustment of the one or more operational parameters of one or more of the first laser source or the at least the second laser source following the ignition of the plasma adjusts at least one of the ignited plasma size, the ignited plasma shape, or the ignited plasma temperature.

36. The system of claim 22, wherein the gas containment element comprises:
a chamber configured to contain a volume of gas.

37. The system of claim 22, wherein the gas containment element comprises:
a plasma cell configured to contain a volume of gas.

38. The system of claim 22, wherein the gas containment element comprises:
a plasma bulb configured to contain a volume of gas.

39. The system of claim 22, wherein the gas containment element contains a gas including at least one of an inert gas, a non-inert gas and a mixture of two or more gases.

40. The system of claim 22, wherein the gas containment element contains a gas including a mixture of a noble gas and one or more trace materials.

41. The system of claim 22, further comprising:
an optical tool characterization system optically coupled to an output of the broadband illumination source subsystem.

42. The system of claim 22, wherein the one or more optical elements are individually adjustable, wherein adjusting the one or more optical elements adjusts at least one of the coupling of the first laser beam to the first region of the optical fiber or the coupling of the at least the second laser beam to the at least the second region of the optical fiber.

43. The system of claim 22, wherein the one or more optical elements are individually adjustable, wherein the first laser beam and the at least the second laser beam are mixable within a region of the optical fiber, wherein adjusting the one or more optical elements or the one or more operational parameters adjusts at least one relative mixing ratio of the first laser beam and the at least the second laser beam within the region of the optical fiber.

* * * * *